(12) United States Patent
Emig et al.

(10) Patent No.: US 6,699,219 B2
(45) Date of Patent: Mar. 2, 2004

(54) FLUID DELIVERY SYSTEMS, INJECTOR SYSTEMS AND METHODS OF FLUID DELIVERY

(75) Inventors: Michael F. Emig, Pittsburgh, PA (US); Klaus Urich, Berlin (DE); Frederick Trombley, III, Gibsonia, PA (US); Joseph B. Havrilla, Pittsburgh, PA (US); Edward J. Rhinehart, Monroeville, PA (US); Gerald W. Callan, Greensburg, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/281,661

(22) Filed: Oct. 28, 2002

(65) Prior Publication Data

US 2003/0060704 A1 Mar. 27, 2003

Related U.S. Application Data (63) Continuation of application No. 09/553,822, filed on Apr. 21, 2000, now Pat. No. 6,471,674.

(51) Int. Cl.$^7$ ............................................. A61M 37/00
(52) U.S. Cl. ..................... 604/131; 604/533; 604/151; 604/246; 604/247; 604/256; 604/257; 604/258
(58) Field of Search .................. 604/131, 43, 284, 604/533, 133, 890.1, 27, 30, 31, 93.01, 118, 151, 152, 154, 164.01, 167.01, 167.02, 167.03, 167.04, 181, 186, 187, 245, 246, 247, 256, 257, 258; 128/DIG. 1, DIG. 12

(56) References Cited

U.S. PATENT DOCUMENTS

| 3,908,652 A | 9/1975 | Weissinger |
| 4,677,980 A | 7/1987 | Reilly et al. |
| 4,944,726 A | 7/1990 | Hilal et al. |
| 5,002,528 A | 3/1991 | Palestrant |
| 5,049,128 A | 9/1991 | Duquette |
| 5,135,489 A | 8/1992 | Jepson et al. |
| 5,188,603 A | 2/1993 | Vaillancourt |
| 5,308,334 A | 5/1994 | Sancoff |
| 5,356,375 A | 10/1994 | Higley |
| 5,360,413 A | 11/1994 | Leason et al. |
| 5,383,858 A | 1/1995 | Reilly et al. |
| 5,423,746 A | 6/1995 | Burkett et al. |

(List continued on next page.)

FOREIGN PATENT DOCUMENTS

| EP | 0 795 342 | 9/1997 |
| WO | WO 99/38562 | 8/1999 |

OTHER PUBLICATIONS

International Search Report for Counterpart PCT Application No.: PCT/US01/12781.

Optistar MR Digital Injection System Operator's Manual, 801900–A (Nov. 1999).

Medrad Spectris MR Injector Operation Manual, pp. 2–1 to 2–18, 4–1 to 4–8 and 6–1 to 6–10 (1996); 92901–T–107, Rev. E.

*Primary Examiner*—Henry Bennett
*Assistant Examiner*—Fadi H. Dahbour
(74) *Attorney, Agent, or Firm*—Gregory L. Bradley; Henry E. Bartony, Jr.

(57) ABSTRACT

A fluid delivery system for delivery of an injection fluid to a patient generally includes a pump system to pressurize the injection fluid, a patient interface in removable fluid connection with the pump system, and a connector in fluid connection between the pump system and the patient interface. The pump system is connected to an inlet of the connector, and the patient interface is removably connected to an outlet of the connector. The connector includes a sealing member at least partly disposed within a housing of the connector that is biased to close the outlet when the patient interface is removed.

5 Claims, 9 Drawing Sheets

U.S. PATENT DOCUMENTS

| | | |
|---|---|---|
| 5,439,451 A | 8/1995 | Collinson et al. |
| 5,501,674 A * | 3/1996 | Trombley, III et al. ..... 604/247 |
| 5,505,707 A | 4/1996 | Manzie et al. |
| 5,569,181 A | 10/1996 | Heilman et al. |
| 5,573,515 A | 11/1996 | Wilson et al. |
| 5,665,074 A | 9/1997 | Kelly |
| 5,685,842 A | 11/1997 | Drivas |
| 5,685,866 A | 11/1997 | Lopez |
| 5,694,686 A | 12/1997 | Lopez |
| 5,755,692 A | 5/1998 | Manicom |
| 5,806,519 A | 9/1998 | Evans, III et al. |
| 5,827,219 A | 10/1998 | Uber, III et al. |
| 5,840,026 A | 11/1998 | Uber, III et al. |
| 5,840,058 A | 11/1998 | Ammann et al. |
| 5,840,068 A | 11/1998 | Cartledge |
| 5,843,037 A | 12/1998 | Uber, III et al. |
| 5,885,216 A | 3/1999 | Evans, III et al. |
| 5,916,197 A | 6/1999 | Reilly et al. |
| 5,947,911 A | 9/1999 | Wong et al. |
| 5,954,695 A | 9/1999 | Sims et al. |
| RE36,648 E | 4/2000 | Uber, III et al. |
| 6,048,335 A | 4/2000 | Mayer |
| 6,063,052 A * | 5/2000 | Uber, III et al. ............. 604/154 |
| 6,096,011 A | 8/2000 | Trombley, III et al. |
| 6,149,627 A * | 11/2000 | Uber, III .................... 604/151 |
| 6,306,117 B1 * | 10/2001 | Uber, III .................... 604/151 |
| 6,344,030 B1 | 2/2002 | Duchon et al. |
| 6,440,107 B1 * | 8/2002 | Trombley, III et al. ..... 604/256 |
| 6,575,930 B1 * | 6/2003 | Trombley, III et al. ..... 604/131 |
| 6,620,134 B1 * | 9/2003 | Trombley, III et al. ..... 604/133 |

* cited by examiner

FLUID DELIVERY SYSTEMS, INJECTOR SYSTEMS AND METHODS OF FLUID DELIVERY

CROSS-REFERENCE TO RELATED APPLICATION

This application is a continuation of application Ser. No. 09/553,822, filed on Apr. 21, 2000, now U.S. Pat. No. 6,471,674, the contents of which are hereby incorporated by reference.

BACKGROUND OF THE INVENTION

The present invention relates to fluid delivery systems, to injector systems, and to methods of delivering fluids, and, more particularly, to multipatient fluid delivery systems, to multipatient injector systems and to methods of multipatient fluid delivery for use in medical procedures in which a fluid is delivered at a relatively high pressure.

In many medical procedures, such as drug delivery, it is desirable to inject a fluid into a patient. Likewise, numerous types of contrast media (often referred to simply as contrast) are injected into a patient for many diagnostic and therapeutic imaging procedures. In some medical imaging procedures (for example, computed tomography (CT), angiography, ultrasound and nuclear magnetic resonance/magnetic resonance imaging (MRI)), it is desirable to deliver a liquid such as contrast medium in a timed fashion under relatively high pressures. Such relatively high pressures and timed boluses are typically achieved through the use of powered injectors.

To, for example, optimize contrast volume delivery, minimize waste of contrast and facilitate injector procedures for operators, fluid delivery systems that are capable of delivering sufficient contrast for multiple injection procedures from a single source of contrast have recently been developed. Examples of such systems are described generally in U.S. Pat. Nos. 5,569,181, 5,806,519, 5,843,037 and 5,885,216, the disclosures of which are incorporated herein by reference. Typically, it is desirable that such fluid delivery systems include a fluid path with a disposable patient interface that is changed/discarded between each patient to reduce the potential for cross-contamination.

A fluid path connector is required to incorporate a removable/disposable patient interface in the fluid path of a fluid delivery or injector system. However, many fluid path connectors used in medical procedures exhibit a number of substantial drawbacks including, for example, difficulty of use and difficulty in maintaining sterility. Moreover, when such connectors are used at high pressures, leakage and failure also become substantial problems.

It is very desirable to develop fluid delivery systems including fluid path connections for use at relatively high pressures that reduce or eliminate the drawbacks associated with current connectors and systems.

SUMMARY OF THE INVENTION

The present invention provides a fluid delivery system for injecting an injection fluid into a patient that includes generally: a first pump system to pressurize the injection fluid; a patient interface in removable fluid connection with the first pump system; and a fluid path in fluid connection between the first pump system and the patient interface. The fluid path preferably includes a connector. The first pump system is in fluid connection with an inlet of the connector. The patient interface is in removable fluid connection with an outlet of the connector. The connector preferably includes a sealing member at least partly disposed within a housing of the connector that is biased to close the outlet when the patient interface is disconnected from the connector. As used herein, the term "connection" and the phrase "fluid connection" encompasses both direct and indirect connection and/or fluid connection.

The sealing member preferably extends from an interior of the housing of the connector when the patient interface is disconnected therefrom to be at least generally flush with the outlet of the connector to facilitate aseptic cleaning of an outward facing surface of the sealing member. The sealing member preferably prevents contaminants from entering the interior of the connector housing when the patient interface is disconnected from the connector. Preferably, an increase of pressure within the connector housing acts to improve a seal created by the sealing member when the patient interface is disconnected from the connector. For example, such a pressure increase can increase the force with which the sealing member is biased to close the outlet of the connector.

In one aspect of the present invention, the first pump system is a syringe that includes sufficient injection fluid for multiple injection procedures. The syringe can, for example, be a prefilled, disposable syringe.

The fluid delivery system can further include a second pump system to pressurize a fluid other than the injection fluid (for example, saline). The second pump system is preferably in fluid connection with the patient interface through the connector.

An outlet of the first pump system is preferably in fluid connection with a first check valve to control flow of fluid into the first pump system. Likewise, an outlet of the second pump system is preferably in fluid connection with a second check valve to control flow of fluid into the second pump system.

The present invention also provides a kit for use in a procedure in which an injection fluid is delivered to a patient. The kit includes generally: a first syringe preferably having a volume to contain sufficient injection fluid for at least two injection procedures; at least one patient interface adapted to be in fluid connection with the patient; and a fluid path adapted to removably connect the patient interface to the first syringe. The fluid path preferably includes a connector having an outlet adapted to removably connect the patient interface thereto. The connector preferably further includes an inlet adapted to connect the connector to the first syringe.

As described above, the connector may include a sealing member at least partly disposed within a housing of the connector that is biased to close the outlet when the patient interface is not attached to the connector. Preferably, the first syringe is prefilled with sufficient injection fluid for at least two injection procedures. Preferably, the kit includes multiple patient interfaces. The kit can also include a second syringe for injecting a fluid (for example, saline) other than the injection fluid.

The present invention also provides an injector system for injection of a fluid into a patient. The injector system includes generally: a powered injector including a first drive member; a first syringe including a first plunger slidably disposed therein, the first syringe being connected to the powered injector such that the first drive member can impart powered motion to the first plunger; a patient interface in removable fluid connection with the first syringe; and a connector as described above. The injector system can further include a second syringe having a second plunger slidably disposed therein. The second plunger is in powered connection with a second drive member of the powered injector. The second syringe can, for example, be adapted to inject saline into the patient. Like the first syringe, the second syringe is preferably in fluid connection with the patient interface through the connector.

The present invention further provides a method of injecting a fluid into multiple patients including the steps of: providing a first pump system containing fluid sufficient to inject at least two patients, the first pump system adapted to pressurize the injection fluid; providing a connector in fluid connection with the first pump system, the connector including a housing having an inlet, an outlet and a sealing member at least partly disposed within the housing, the sealing member being biased to close the outlet to prevent fluid flow out of or into the first pump system; providing a patient interface operable to be removably connected to the outlet of the connector to deliver the fluid to a patient; removably connecting the patient interface to the outlet of the connector, whereby the patient interface opens the sealing member to create a fluid path from the first pump system to the patient; and injecting fluid from the first pump system into the patient. In one aspect, the first pump system is a syringe prefilled with sufficient injection fluid for at least two injection procedures.

The method preferably further includes the steps of: removing the patient interface after the injection of injection fluid into the patient; providing a second patient interface; aseptically treating the connector; and connecting the second patient interface to the outlet of the connector.

The present invention, together with its attendant advantages, will be further understood by reference to the following detailed description taken in conjunction with the accompanying drawings.

DETAILED DESCRIPTION OF THE INVENTION

Figure 1:
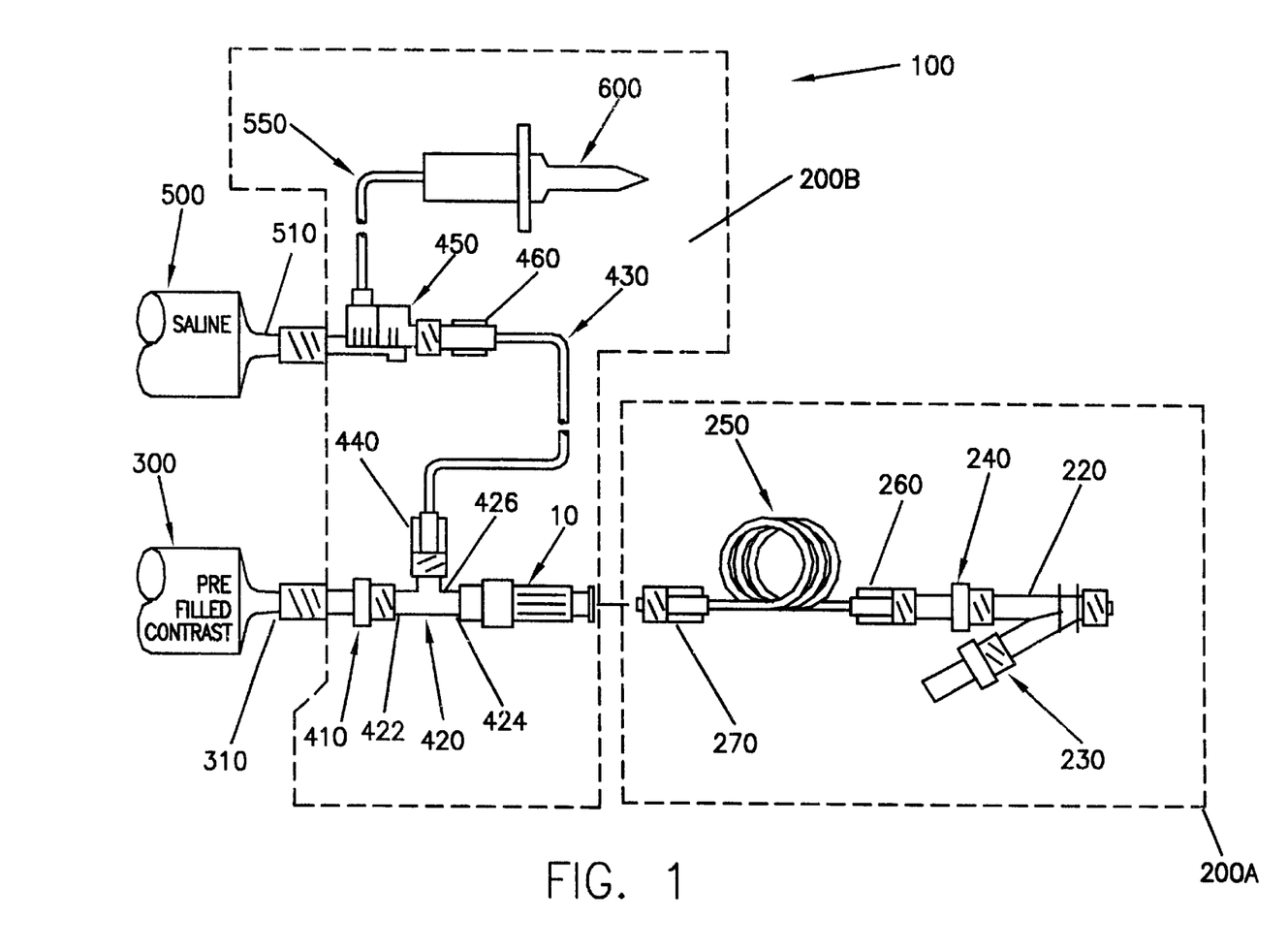
FIG. 1 illustrates an embodiment of a fluid delivery system of the present invention in which a patient interface is disconnected.

FIG. 1 illustrates an embodiment of a fluid (for example, contrast media) delivery system 100 of the present invention that is particularly suitable for use in MRI. However, the fluid path delivery system of the present invention is equally applicable in other injection procedures, including, for example, ultrasound, CT and angiography.

The fluid path of fluid delivery system 100 preferably includes a disposable patient interface 200a in releasable fluid connection with an interval fluid path 200b. Interval fluid path 200b is preferably in fluid connection with an outlet 310 of a pumping system, such as an injector-powered syringe 300. An example of a powered injector and syringe suitable for use in the present invention is the Spectris® Injector available from Medrad, Inc. of Indianola, Pa., which is disclosed in U.S. Reissue Pat. No. 36,648, the contents of which are hereby incorporated by reference. Other suitable injectors are disclosed in U.S. Pat. Nos. 4,677,980 and 5,383,858, the contents of which are incorporated herein by reference.

Although the fluid delivery systems of the present invention are described herein with the use of syringe pumps, other pumping systems, such as rotary pumps, in-line pumps and gear pumps, are also suitable for use in the present invention. For example, the pumps disclosed in U.S. Pat. Nos. 5,916,197 and 5,827,219, the disclosures of which are hereby incorporated by reference, may be suitable for use with the present invention.

In the embodiment of FIG. 1, disposable patient interface 200a preferably comprises a connector 220 for attachment, for example, to an intravenous (IV) catheter (not shown). Connector 220 may include a y-connector port 230 for "needleless" or "needle-free" aspiration, as known in the art. For example, an operator may aspirate through port 230 after the catheter is inserted into the patient to ensure that the catheter is properly placed within a vein. Connector 220 is preferably in fluid connection with a check valve 240 or other suitable means to ensure unidirectional flow of the medium into the patient. Check valve 240 is in fluid connection with flexible tubing 250 via, for example, a Luer connection 260 as known in the art. Flexible tubing 250 is preferably in fluid connection (via, for example, a Luer connection 270) with the outlet of a connector 10 of interval fluid path 200b.

Connector 10 is preferably suitable for use at the relatively high pressures experienced in the powered injection procedure without leakage or failure. Moreover, connector 10 is preferably suitable for repeated use at the pressures experienced in such powered injection procedures. In one aspect, for example, connector 10 is preferably suitable to withstand a pressure of at least approximately 300 psi without leakage or failure. In general, pressures of up to approximately 300 psi can be experienced in MRI, CT and ultrasound contrast delivery procedures.

If connector 10 and per patient interface 200a of the present invention are to be used in connection with other procedures, such as angiography, higher pressure specifications are preferred. In general, the highest pressures experienced in current powered injection procedures are experienced in angiography, in which pressures can be as high as approximately 1200 to approximately 1400 psi. Thus, if the flow path of the present invention is to be used in connection with an angiography procedure, connector 10 is preferably suitable to withstand a pressure of at least approximately 1200 psi (and, more preferably, at least approximately 1400 psi) without leakage or failure.

As used herein to describe fluid delivery system 100, the term "rearward" refers generally to a direction (along the longitudinal axis of syringe 300) toward the end of syringe 300 opposite syringe outlet 310. The term "forward" refers generally to a direction toward syringe outlet 310.

In general, connector 10 is used in the present invention to removably connect per-patient interface 200a to interval fluid path 200b of fluid delivery system 100, As illustrated in FIG. 1, the releasable nature of connector 10 of the present invention allows patient interface 200a to be disconnected from connector 10 (for example, via Luer connection 270) so that, for example, patient interface 200a may be discarded, preferably after each injection procedure. The removable or disposable nature of patient interface 200a assists in preventing cross contamination between patients. The components of interval fluid path 200b, including connector 10, are preferably discarded at periodic intervals (for example, after use with several doses of injection fluid or after a predetermine amount of time) to preclude contamination of the fluid sources and cross-contamination between patients.

As described above, the inlet of connector 10 is preferably in fluid communication with an outlet or syringe tip 310 of syringe 300. In the embodiment of FIG. 1, a one-way check valve 410 connects syringe outlet 310 to a port 422 of a three-port T-connector 420. A second port 424 of T-connector 420 is connected to connector 10, while a third port 426 of T-connector 420 is preferably in fluid connection with a second syringe 500. In the case that saline or any fluid other than injection fluid of syringe 300 is not needed, connector 10 can be connected to check valve 410 without intermediate three-port connector 420. Syringe 300 and syringe 500 are preferably discarded on the same interval as interval fluid path 200b.

In the embodiment of FIG. 1, port 426 is preferably connected to tubing 430 at one end thereof via, for example, a Luer connection 440. A second end of tubing 430 is preferably connected to the outlet of a dual check valve 450 (or a transfer valve/check valve assembly) via, for example, a Luer connection 460. One inlet of dual check valve 450 is preferably connected to a source of saline 700 (see FIG. 2A) via, for example, tubing 550 and spike 600 (for example, a hyperal spike). The other inlet of dual check valve 450 is preferably connected to outlet 510 of syringe 500.

Figure 2A:
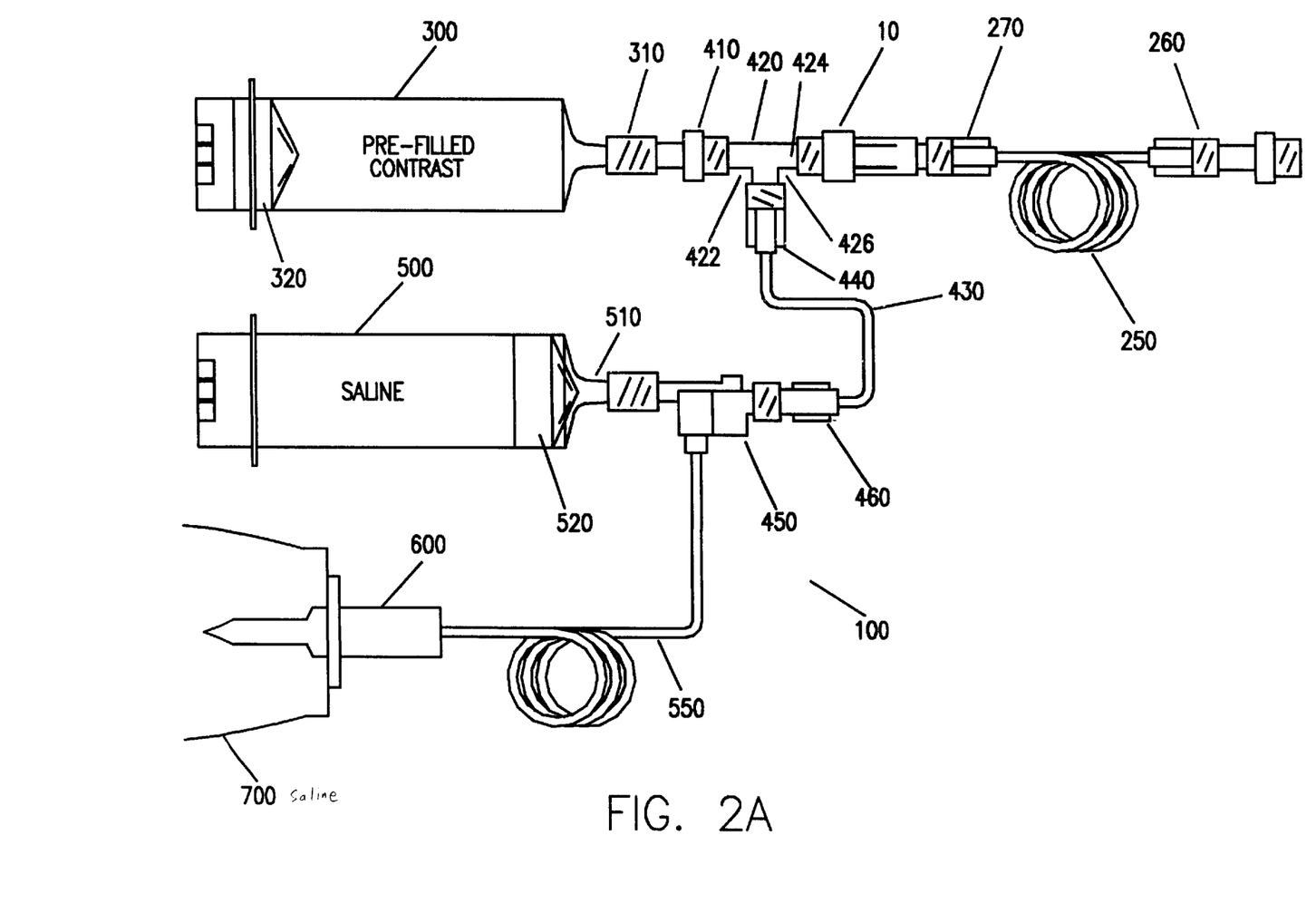
FIG. 2A illustrates an embodiment of a fluid delivery system of the present invention in a fully connected state.

Operation of fluid delivery system 100 will be described with reference to FIGS. 2A through 2F. FIG. 2A illustrates fluid delivery system 100 in a fully connected state. In this embodiment, syringe 300 is preferably prefilled with sufficient contrast medium for two or more injection procedures. In one embodiment, for example, contrast syringe 300 had a volume of approximately 55 to approximately 60 ml. Typically, 10 to 20 ml of contrast medium are injected in each MRI procedure.

A number of advantages are provided by multi-dose syringe 300 of fluid delivery system 100 as compared to currently available systems. Like other multiple dosing or multiple patient systems, fluid delivery system 100 enables the delivery of one or more doses of injection fluid to one or more patients, with the attendant advantages of multiple dosing. Unlike other multiple dosing systems, however, multiple dose syringe 300 and the associated fluid path of the present invention enables multiple dosing without requiring specialized equipment. In that regard, multiple dose syringe 300 is easily designed for connection to many types of injectors (with or without the use of an adapter) as known in the art.

Furthermore, use of multiple dose syringe 300 reduces operator setup time as compared to other multiple dosing systems. Preferably, syringe 300 is prefilled (before delivery to the operator) with the injection fluid to further reduce operator setup time and to reduce the potential for contamination during setup. Prefilled syringes are discussed generally in PCT Publication No. WO 98/20920, the disclosure of which is incorporated herein by reference.

Figure 2B:
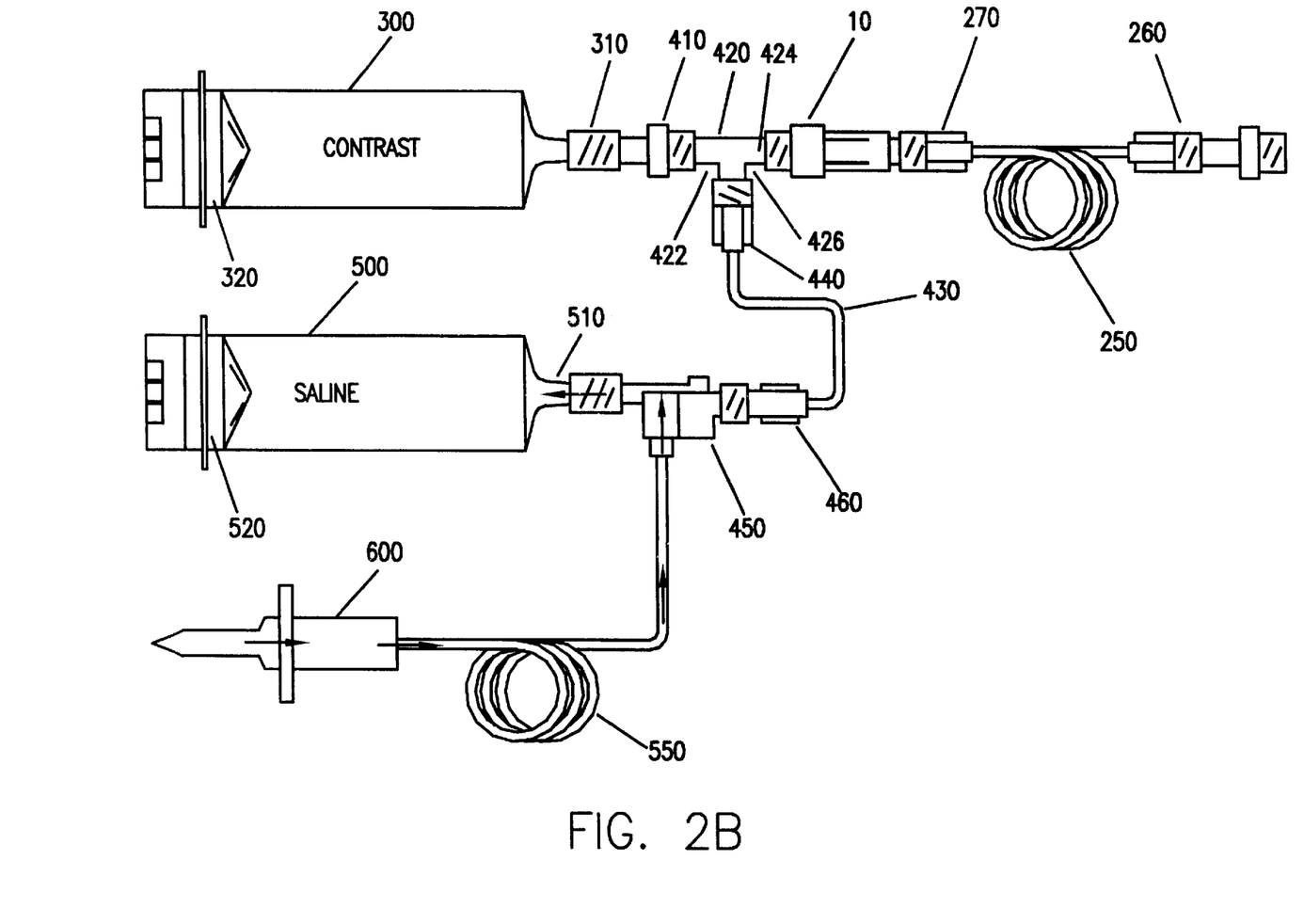
FIG. 2B illustrates the fluid delivery system of FIG. 2A in which saline is drawn into a saline syringe.

In FIG. 2A, plunger 520 of saline syringe 500 is advanced to its fully forward position. FIG. 2B illustrates the rearward movement of plunger 520 to draw saline into syringe 500 as represented by the flow arrows of FIG. 2B. When plunger 520 is drawn rearward as represented in FIG. 2B, dual check valve 450 prevents fluid from tubing 430 from being drawn into saline syringe 500.

Figure 2C:
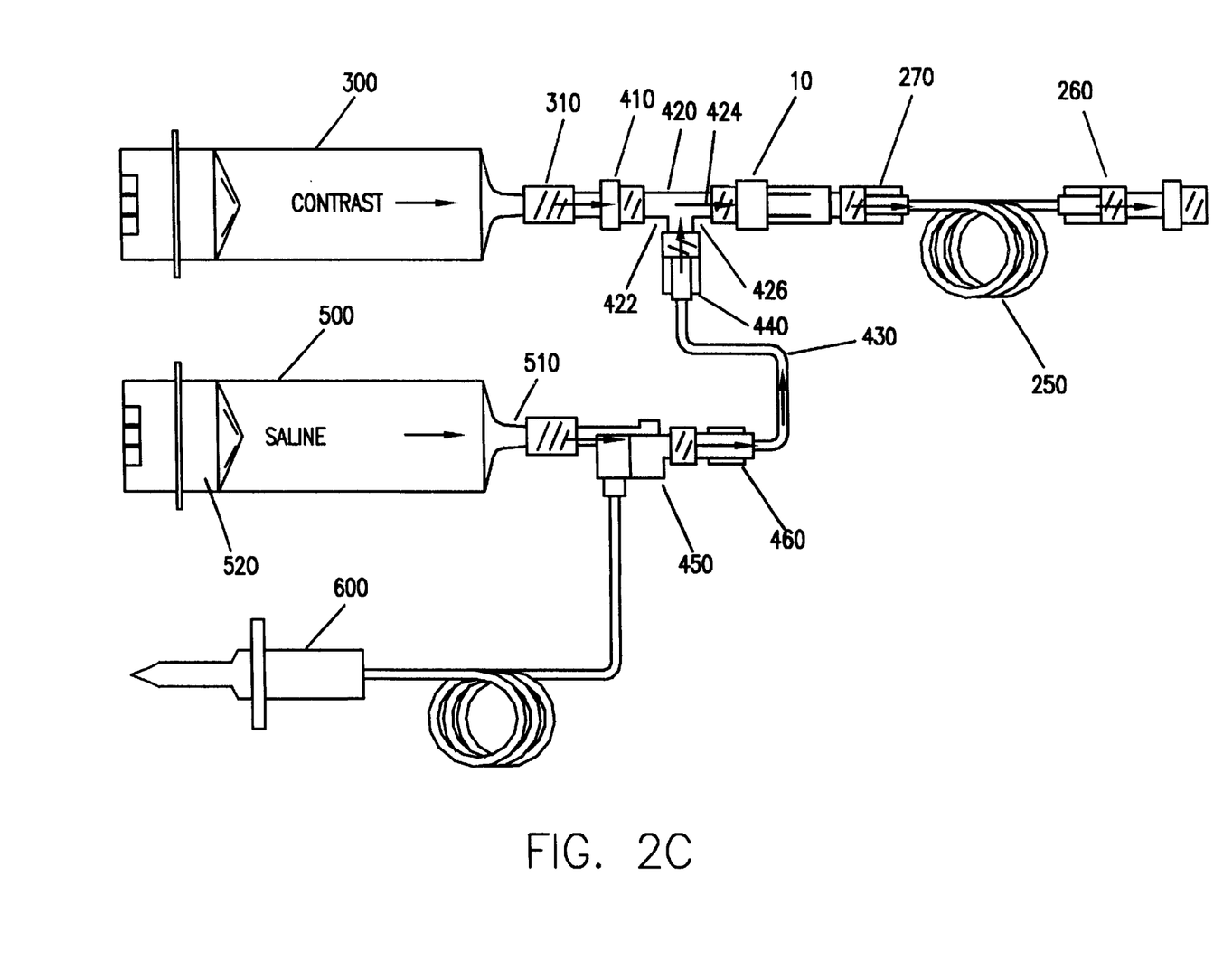
FIG. 2C illustrates the fluid delivery system of FIG. 2A in which the fluid path is primed.

In FIG. 2C, forward motion of plunger 520 causes saline to flow through the fluid path, including tubing 430 and patient interface 200, as represented by the solid flow arrows. Such "priming" of the fluid delivery path with saline is preferred, for example, to remove air from the fluid path and minimize wastage of contrast medium. Check valve 410 prevents saline from entering contrast syringe 300. Plunger 320 of contrast syringe 300 is also preferably advanced sufficiently to prime the fluid path between syringe 300 and check valve 410 for injection of contrast. In that regard, a small amount of contrast can be injected into the fluid path as illustrated by the dashed flow arrows in FIG. 2C to remove any air between syringe 300 and check valve 410.

After priming of fluid delivery system 100 as described above, the patient interface 200 is connected to the patient by means of, for example, a catheter. An operator may then, for example, begin a slow flow of saline to assist in assuring that the vein in which the catheter (not shown) is placed remains open (sometime referred to as a keep-vein-open or KVO process). Before injection of contrast, the flow of saline is preferably stopped.

Figure 2D:
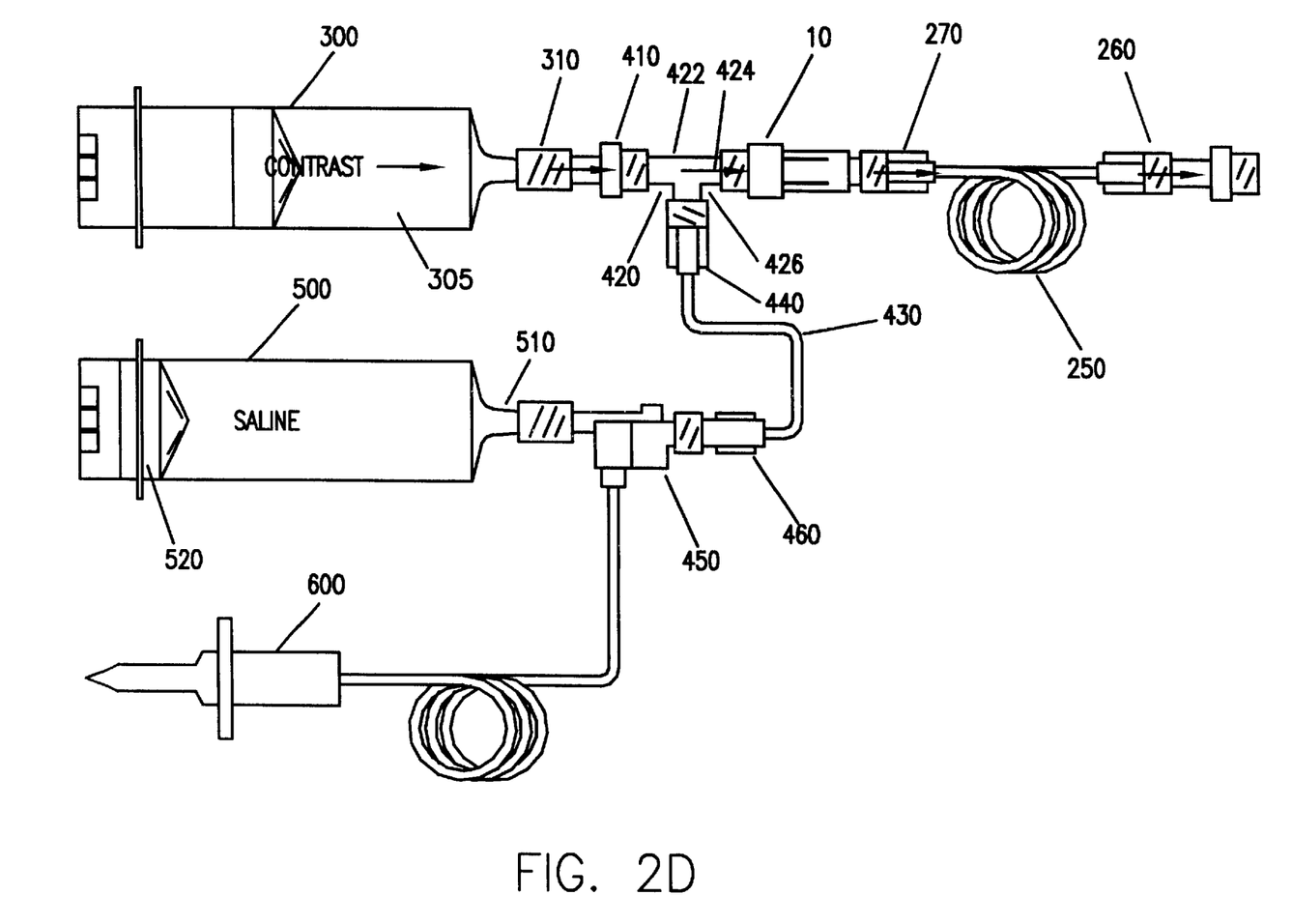
FIG. 2D illustrates the fluid delivery system of FIG. 2A in which a bolus of contrast is being injected.
Figure 2E:
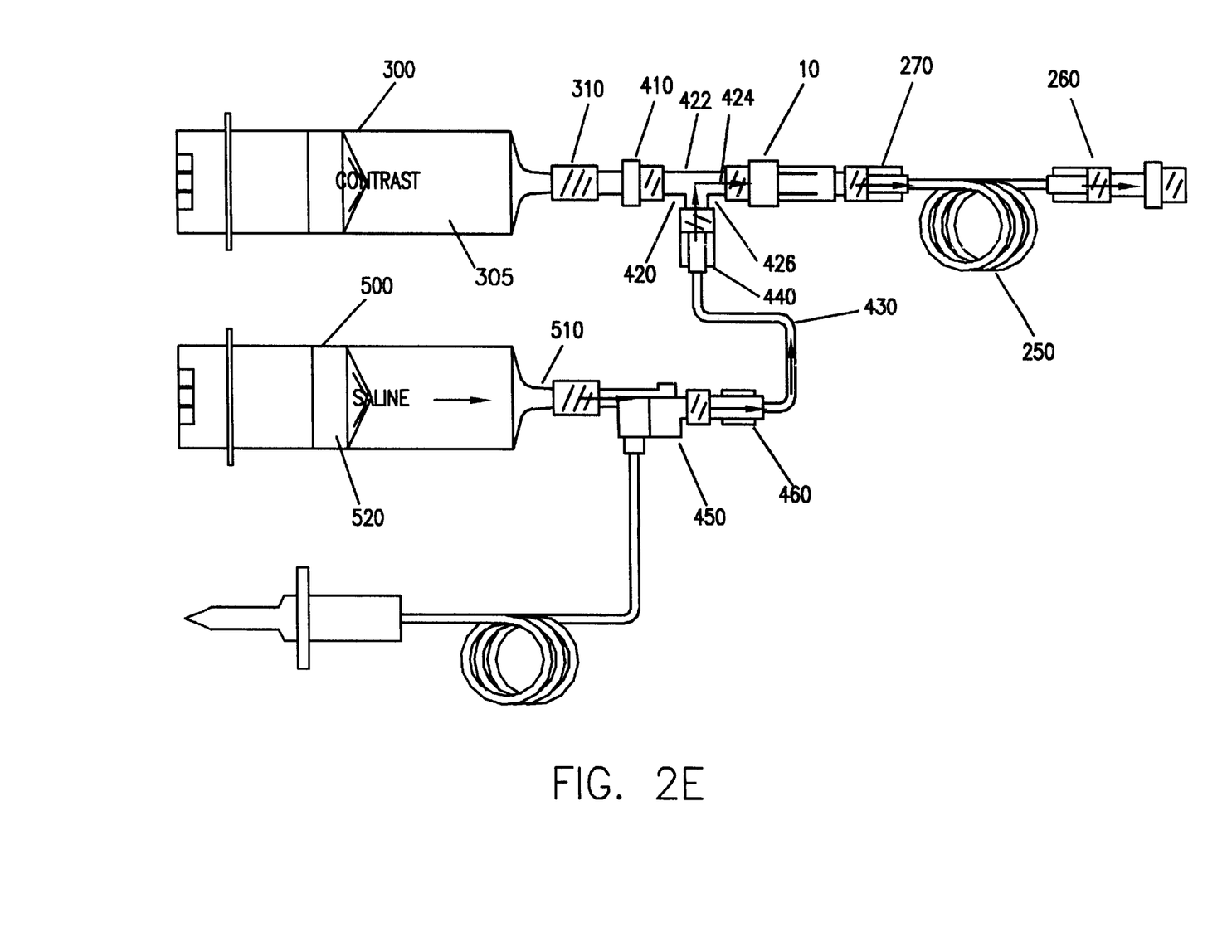
FIG. 2E illustrates the fluid delivery system of FIG. 2A in which the fluid path is being flushed with saline.

Injection of a volume (i.e., infusion or bolus) of contrast is illustrated in FIG. 2D. During injection of contrast, plunger 310 is preferably advanced in a manner to provide a predetermined flow rate and volume of contrast. The flow of contrast through the fluid path is represented by the dashed arrows in FIG. 2D.

After injection of a volume of contrast as illustrated in FIG. 2D, the fluid path is preferably flushed with saline at approximately the same flow rate as the contrast injection. The flow rate of the saline flush is preferably matched to approximately the same flow rate at which the contrast was injected to assist in assuring that the entire amount of contrast injected from syringe 300 will travel through the fluid path (including patient interface 200) and the patient as, for example, a "tight" bolus with the desired flow rate. Generally, contrast for use in MRI and other injection procedures is quite expensive and it is desirable to reduce waste thereof wherever possible by, for example, ensuring that no contrast remains in any portion of the fluid delivery path. Moreover, the timing of the delivery of a predetermined volume of contrast bolus is typically very important in optimizing image enhancement in the region of interest.

Figure 2F:
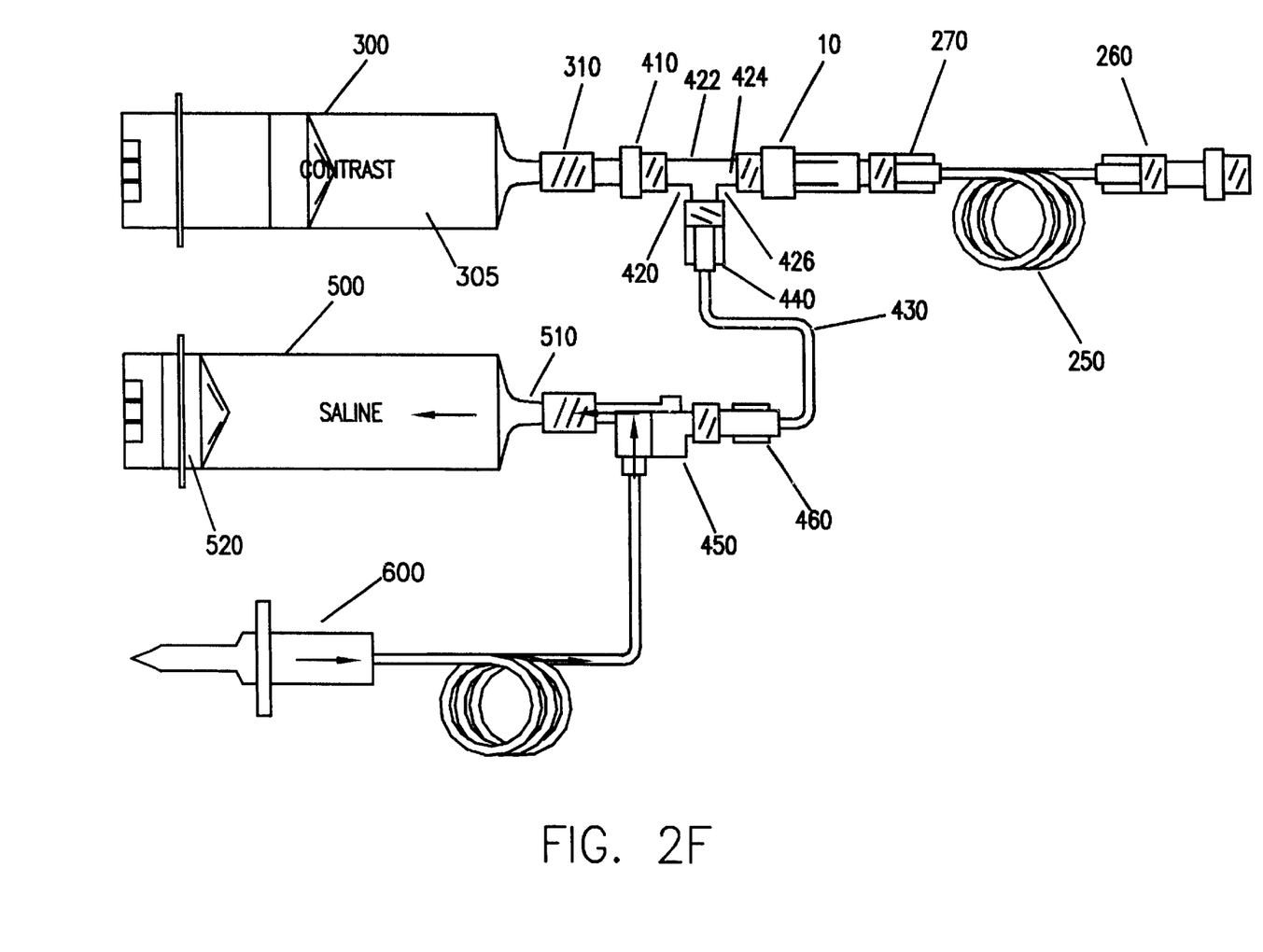
FIG. 2F illustrates the fluid delivery system of FIG. 2A in which saline is once again drawn into the saline syringe after an injection procedure as described in FIGS. 2A through 2E.

After flushing with saline, saline syringe 500 can be refilled as illustrated in FIG. 2F by retracting plunger 520. Once again, dual check valve 450 prevents fluid from tubing 430 from entering saline syringe 500.

Additional injection procedures can then be conducted for the same patient through the patient interface 200 in the same or similar manner as described above. If a different patient is to be injected, the patient interface 200 is removed from the connector and preferably discarded, the connector is aseptically cleaned and a new patient interface is connected to the connector. The fluid path and the patient interface may then be primed, the new patient interface connected to the new patient and the fluid injection performed.

Although described above for use in connection with prefilled syringes, the present invention is not limited to the case of prefilled syringes. Contrast can, for example, be periodically loaded into a syringe from a source of contrast medium in a similar manner as the loading of saline into saline syringe 550 as illustrated in FIGS. 2B and 2F. Moreover, as discussed above, the contrast and/or saline pumping system need not include syringes. Other types of pumping systems, such as rotary pumps, in-line pumps and gear pumps, are suitable for use in the present invention. Such pumping systems can, for example, be connected to fluid sources such as bags or bottles, which may contain contrast, saline and/or therapeutic drugs. Furthermore, more than two pumping systems can be in fluid connection with connector 10 using fluid connections (for example, multi-port connectors) as known in the art.

As described above, the disposable nature of patient interface 200a assists in preventing cross contamination between patients in the case that multiple injections are performed using a single prefilled contrast syringe or other pumping system/source of contrast. Furthermore, a relatively long length of tubing 250 is preferably used in patient interface 200a to further reduce the risk of cross-contamination. In that regard, migration of infectious agents through patient interface 200a to reach connector 10 can be greatly reduced or eliminated in use over a certain period of time by lengthening tubing 250. In one embodiment, for example, tubing 250 had a length of approximately 96 inches.

Because several different patient interfaces 200a will be connected to and disconnected from connector 10 over the course of several injection procedures, connector 10 is preferably adapted to facilitate aseptic cleaning or treatment thereof while in a disconnected state. Moreover, as discussed above, connector 10 is preferably suitable to withstand the relatively high pressures used in various injection procedures without failure. Preferably, connector 10 is suitable to withstand even the excessive pressure that would be generated if a pump system (for example, one of or both of syringes 300 and 500) was erroneously engaged when patient interface 200a was disconnected from connector 10.

Figure 3:
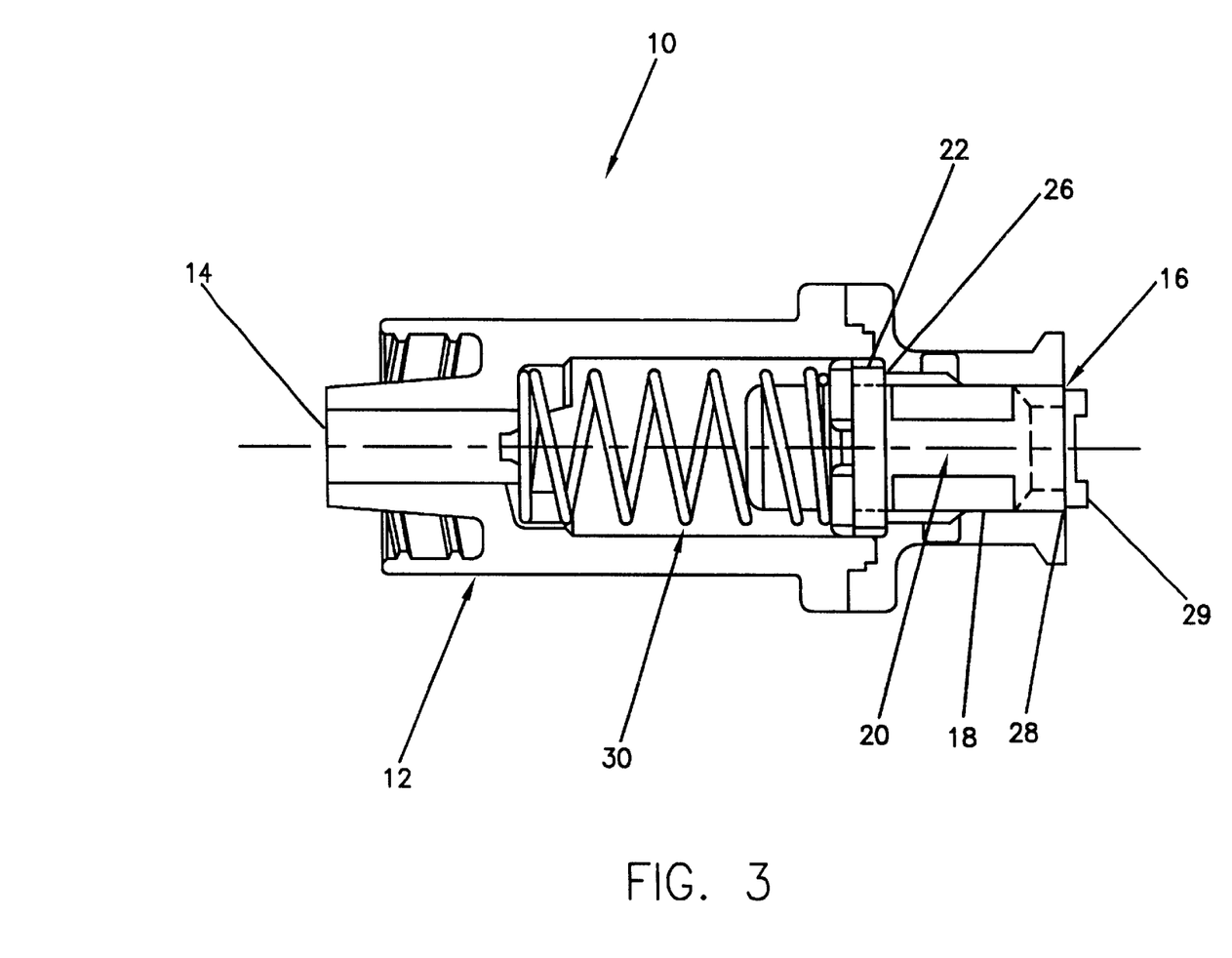
FIG. 3 illustrates a side, cross-sectional view of a fluid path connector suitable for use in the present invention.

An embodiment of a connector 10 suitable for use in the present invention is illustrated in FIG. 3. Connector 10 includes a housing 12, an inlet 14 and an outlet 16. Outlet 16 is defined generally by a passage or channel 18 formed in housing 12. A sealing member such as a pin valve member 20 is biased outwardly within channel 18 to fill channel 18 and thereby seal outlet 16. A base 22 of pin valve member 20 can, for example, be biased against an annular sealing ring 26. Pin valve member 20 can be biased in an outward, sealing direction by, for example, a helical spring 30 disposed within housing 12. Pin valve member 20 can further include a wiper seal 28 that seals the outer portion of channel 18 when pin valve member 20 is biased in a closed position. Seal 28 substantially prevents contaminants from entering the interior of housing 12 when patient interface 200a is disconnected from connector 10.

The exterior surface of channel 18 is preferably tapered to accept the male portion of a Luer connection as known in the art. In general, the male portion of Luer connector 270 contacts a forward portion of pin valve member 20. Application of rearward force by an operator causes pin valve member 20 to move rearward and the male portion of Luer connector 270 to enter channel 18. Via the Luer connection, patient interface 200a is connected to connector 10 to allow fluid to flow therethrough. As described above, port 424 of T-valve 420 is preferably connected to inlet 14 of connector 10.

In general, aseptic cleaning of connector 10 is facilitated by the position of the top surface of pin valve member 20 relative to outlet opening 16. In that regard, the top surface of a sealing member such as pin valve member 20 is preferably flush with or extends outwardly from outlet opening 16. A material carrying a disinfectant (for example, a cotton ball) can easily clean the entire surface of pin valve member 20. Moreover, because channel 18 is normally in a closed/sealed state, the interior of housing 12 is substantially protected from contamination from any source in the surrounding environment (whether airborne or via fluid or other contact) when patient interface 200a is disconnected from connector 10.

Connectors 10 suitable for use in the present invention include the Filtertek Needlefree Connector, Product No. 68800, available from Filtertek, Inc. of Hebron, Ill. See U.S. Pat. No. 5,360,413, the disclosure of which is incorporated herein by reference. Such connectors are designed as "needle-free" connectors to be attached directly to a male Luer tip fitting of a manual syringe for use in relatively low-pressure injections. In the present invention, however, the orientation of connector 10 is reversed from the case of its normal use in that one or more pumping systems (for example, syringes 300 and 500) are connected to inlet 14, which is normally the outlet in conventional use.

Other connectors suitable for use in the present invention include the ULTRASITE® valve available from B. Burron Medical of Allentown, Pa. (see U.S. Pat. No. 5,439,451); the CLAVE™ connector available from ICU Medical Inc. of San Clemente, Calif. (see U.S. Pat. Nos. 5,685,866 and 5,694,686); and the ALARIS SMARTSITE™ connector available from Alaris Medical Systems of San Diego, Calif. In each case, the orientation/direction of flow of connector 10 as used in the present invention is reversed from the standard use thereof. Moreover, modifications, such as reinforcement of connector housing, may be required for use of the connector 10 at high pressure.

Connectors such as connector 10 that include an outlet (as oriented for use in the present invention) and a sealing member that is biased in a closed position are particularly suited for use in the case that a patient interface is to be removably attached to a pumping system in a powered injection procedure. For example, in addition to the advantages described above, connector 10 will prevent loss of contrast even if syringe 300 is erroneously engaged when patient interface 200a is disconnected from connector 10. Indeed, in the orientation of connector 10 in the present invention, increased pressure within housing 12 acts to create an even stronger seal of channel 18 by pin valve member 20. Connector 10 is thus suitable for repeated use at relatively high pressures while maintaining a leakproof seal whether patient interface 200a is connected or disconnected thereto.

In several experiments, the needle-free connector of Filtertek, Inc. withstood pressures of approximately 500 psi before leakage and/or failure. Such connectors can easily be adapted for use at higher pressures by, for example, increasing the thickness of the walls of housing 12.

Figure 4:
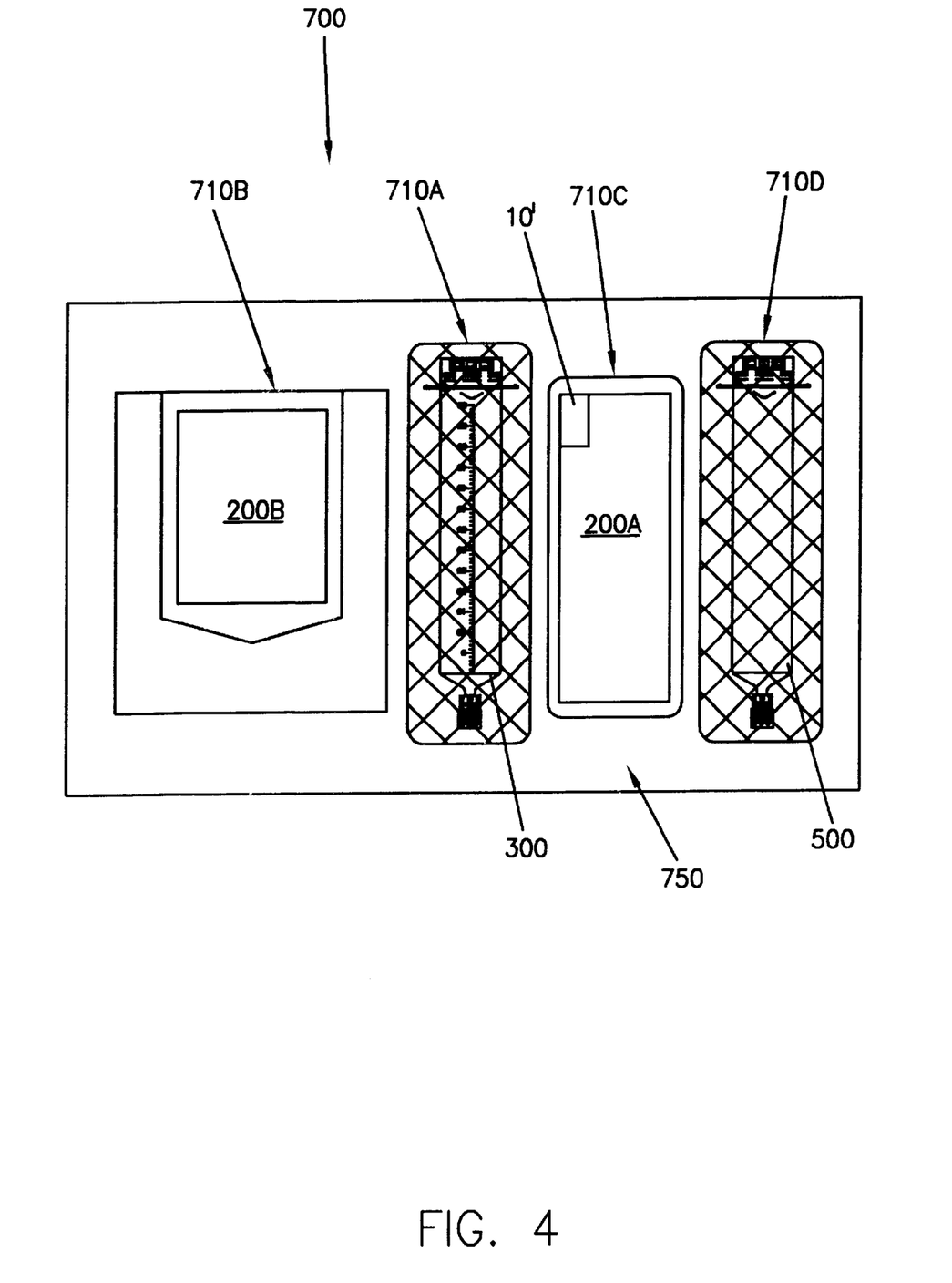
FIG. 4 illustrates a plan view of a packaged kit of the present invention.

FIG. 4 illustrates a packaged kit 700 for use in the present invention. In this aspect of the present invention, kit 700 preferably includes syringe 300 (in compartment 710a) that is preferably prefilled with sufficient injection fluid for two or more injection procedures. Kit 700 also preferably includes interval fluid path 200b (in compartment 710b) and at least one per-patient disposable interface 200a (in compartment 710c).

Patient interface 200a preferably includes at least one connector 10' for removable connection of a patient interface 200a to syringe 300. Preferably, connector 10' is of the type discussed above in connection with connector 10. However, other connectors are suitable for use in kit 700. For example, such a connector is described in PCT Publication No. WO 99/38562, the disclosure of which is incorporated herein by reference.

Preferably, kit 700 includes a plurality of patient interfaces 200a. In that regard, kit 700 preferably includes at least as many patient interfaces 200b as injection fluid doses contained in syringe 300.

Kit 700 can, for example, be packaged in a polymeric form tray/lid combination 750 as known in the packaging arts. In the embodiment of FIG. 4, kit 700 is intended for use in MRI procedures and preferably further includes saline syringe 500 (in compartment 710d).

To further reduce operator setup time and the potential for contamination during setup, syringes 300 and/or syringe 500 can be connected (removably or permanently) to interval fluid path 200b (as illustrated in FIGS. 2A through 2F) in kit 700 before delivery/shipment thereof. Permanently connecting syringe 300 to interval fluid path 200b also may discourage reuse/refilling of syringe 300 after its designed interval of use (for example, after two or three injection procedures) which may reduce the potential for patient cross-contamination.

Although the present invention has been described in detail in connection with the above examples, it is to be understood that such detail is solely for that purpose and that variations can be made by those skilled in the art without departing from the spirit of the invention. The scope of the invention is indicated by the following claims rather than by the foregoing description. All changes to the present invention that fall within the meaning and range of equivalency of the claims are to be embraced within their scope.

What is claimed is:

1. A fluid delivery system comprising:

a first pump system comprising a prefilled syringe including sufficient injection fluid for multiple injection procedures;

a second pump system comprising a syringe operable to be filled with an amount of injection fluid sufficient for at least one injection procedure;

a patient interface in removable fluid connection with the first and second pump systems;

a fluid path in fluid connection between the first and second pump systems and the patient interface, the fluid path comprising a connector comprising a housing defining a first inlet, a second inlet and an outlet and a sealing member at least partially disposed within the housing, the sealing member being adapted to extend outward from an interior of the housing of the connector to be at least generally flush with the outlet of the connector to facilitate cleaning of an outward facing surface of the sealing member and being biased to close the outlet when the patient interface is disconnected from the connector, the first and second pump systems being in fluid connection with the respective first and second inlets of the connector and the patient interface being in removable fluid connection with the outlet of the connector;

a first check valve in fluid connection between an outlet of the syringe of the first pump system and the first inlet of the connector; and a second check valve in fluid connection between an outlet of the syringe of the second pump system and the second inlet of the connector, the first and second check valves operable to control flow of fluid with respect to the respective first and second pump systems.

2. The fluid delivery system of claim 1 wherein the sealing member substantially prevents contaminants from entering the interior of the connector housing when the patient interface is disconnected from the connector.

3. The fluid delivery system of claim 1 wherein an increase of pressure within the connector housing acts to improve a seal created by the sealing member when the patient interface is disconnected from the connector.

4. The fluid delivery system of claim 3 wherein the increase in pressure increases a force with which the sealing member is biased to close the outlet of the connector.

5. The fluid delivery system of claim 1, further comprising a spike member in fluid connection with the syringe of the second pump system, the spike member operable to be inserted into a fluid container.

* * * * *